(12) United States Patent
Owen et al.

(10) Patent No.: US 10,813,620 B2
(45) Date of Patent: Oct. 27, 2020

(54) METHOD AND SYSTEM FOR ENHANCED ULTRASOUND IMAGE ACQUISITION USING ULTRASOUND PATCH PROBES WITH INTERCHANGEABLE BRACKETS

(71) Applicant: General Electric Company, Schenectady, NY (US)

(72) Inventors: Cynthia Owen, Powhatan, AR (US); Alan Tai, Phoenix, AZ (US); Menachem Halmann, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 595 days.

(21) Appl. No.: 15/685,876

(22) Filed: Aug. 24, 2017

(65) Prior Publication Data

US 2019/0059848 A1 Feb. 28, 2019

(51) Int. Cl.
*A61B 8/00* (2006.01)
*A61B 8/08* (2006.01)

(52) U.S. Cl.
CPC ............ *A61B 8/0833* (2013.01); *A61B 8/085* (2013.01); *A61B 8/4236* (2013.01); *A61B 8/4281* (2013.01); *A61B 8/48* (2013.01); *A61B 8/4461* (2013.01); *A61B 8/461* (2013.01); *A61B 8/467* (2013.01)

(58) Field of Classification Search
CPC .................................................. A61B 8/4236
See application file for complete search history.

(56) References Cited

U.S. PATENT DOCUMENTS

| 7,857,763 | B2 | 12/2010 | Tai |
| 8,414,495 | B2 | 4/2013 | Halmann et al. |
| 2010/0168577 | A1* | 7/2010 | Vezina ............... A61B 5/02028 600/443 |
| 2011/0087107 | A1 | 4/2011 | Lindekugel et al. |
| 2017/0265946 | A1* | 9/2017 | Ramachandran .. A61B 1/00013 |
| 2017/0296139 | A1* | 10/2017 | Giaya .................... G16H 40/67 |
| 2018/0153504 | A1* | 6/2018 | Herickhoff ............. A61B 8/085 |

OTHER PUBLICATIONS

Sherman, Garry, DPM, "Patch Based Ultrasound: A New Dimension in Therapeutic Ultrasound," Podiatry Management, www.podiatrym.com, Circle #160, Jun./Jul. 2010, pp. 168-169.

* cited by examiner

*Primary Examiner* — Rochelle D Turchen
(74) *Attorney, Agent, or Firm* — McAndrews, Held & Malloy, Ltd.; Jacob Groethe; David Bates

(57) ABSTRACT

A system includes an ultrasound patch probe and brackets having a body and a base. The body includes a coupler and a hollow interior portion. The coupler is operable to receive the probe at a pre-defined ultrasound acquisition angle. The coupler defines a probe opening to provide the probe access to the hollow interior portion of the body. The coupler of each of the brackets is arranged to receive the probe at a different pre-defined ultrasound acquisition angle. The base surrounds a perimeter of the body and defines a bracket opening that extends through the base to provide access to the hollow interior portion of the body. The base includes a bottom surface operable to be secured against skin of a patient. The ultrasound patch probe is communicatively coupled to an ultrasound imaging system and detachably coupleable to the coupler of any selected one of the brackets.

20 Claims, 9 Drawing Sheets

METHOD AND SYSTEM FOR ENHANCED ULTRASOUND IMAGE ACQUISITION USING ULTRASOUND PATCH PROBES WITH INTERCHANGEABLE BRACKETS

CROSS-REFERENCE TO RELATED APPLICATIONS/INCORPORATION BY REFERENCE

[Not Applicable]

FIELD

Certain embodiments of the disclosure relate to ultrasound imaging. More specifically, certain embodiments of the disclosure relate to a method and system for enhanced ultrasound image acquisition using ultrasound patch probes with replaceable and/or interchangeable brackets having a variety of acquisition angles.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image. Ultrasound examinations are typically performed by an ultrasound operator placing an ultrasound transducer on a body surface and manipulating the ultrasound transducer about the body surface to manually control the acquisition of ultrasound image data. The manual manipulation of the ultrasound transducer is not ideal for prolonged ultrasound image data acquisition. Instead, an ultrasound patch probe may be secured in a fixed position on the body surface of a patient for ultrasound image data acquisition over an extended period of time.

Ultrasound image acquisition may be enhanced in certain ultrasound imaging modes and/or applications by optimizing an angle of insonation (i.e., the angle between the ultrasound beam and the target reflector). For example, a blood flow velocity measurement may be estimated using a Doppler ultrasound imaging mode. The Doppler equation shows that virtually no Doppler signal is detected when an angle of insonation is at right angles to the direction of the blood flow and that the maximum detectable Doppler signal is detected when the Doppler beam is parallel to the direction of blood flow. Moreover, some studies have shown that larger angles of insonation, particularly angles of insonation greater than 60 degrees, result in an increase in velocity measurement errors. Ultrasound patch probes are typically secured to the skin of a patient such that the ultrasound beam is substantially perpendicular to the skin of the patient. Peripheral vessels, however, typically lie generally parallel to the skin of a patient.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method for enhancing ultrasound image acquisition using ultrasound patch probes with interchangeable brackets having a variety of acquisition angles is provided, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
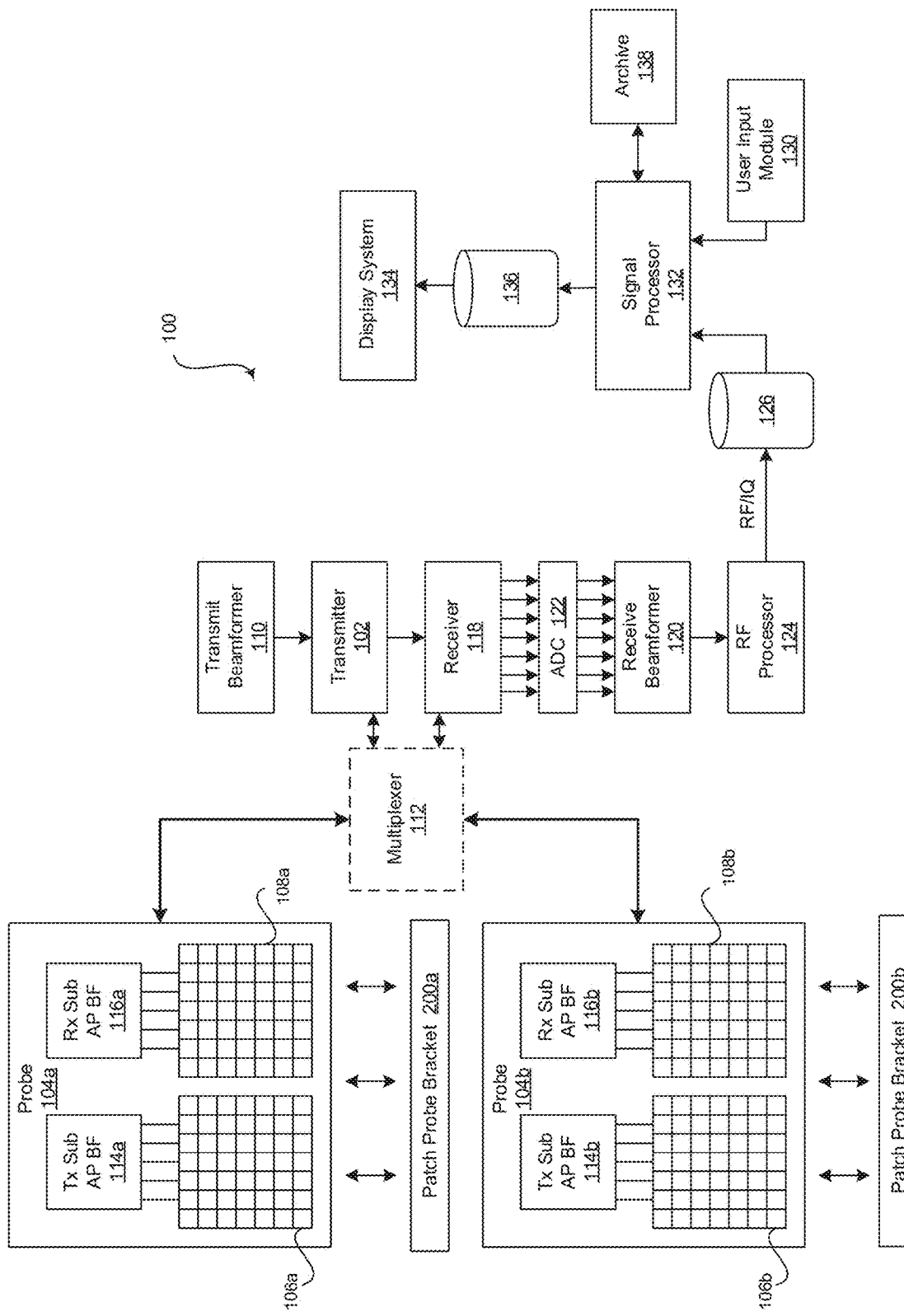
FIG. 1 is a block diagram of an exemplary ultrasound system having ultrasound patch probe(s) for attachment to a patient via ultrasound patch probe bracket(s) having a selected ultrasound acquisition angle, in accordance with various embodiments.

Certain embodiments may be found in a method and system for enhancing ultrasound image acquisition using ultrasound patch probes with interchangeable brackets having a variety of acquisition angles. For example, aspects of the present disclosure have the technical effect of acquiring ultrasound image data via an ultrasound patch probe at a desired angle of insonation by selecting one of a plurality of ultrasound patch probe brackets having an appropriate ultrasound acquisition angle, wherein the ultrasound patch probe brackets have different ultrasound acquisition angles.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present disclosure. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the disclosure, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 having ultrasound patch probe(s) 104a, 104b for attachment to a patient via ultrasound patch probe bracket(s) 200a, 200b having a selected ultrasound acquisition angle, in accordance with various embodiments. Referring to FIG. 1, there is shown ultrasound patch probe brackets 200a, 200b and an ultrasound system 100 comprising a transmitter 102, ultrasound patch probes 104a, 104b, a transmit beamformer 110, a multiplexer 112, a receiver 118, a receive beamformer 120, a RF processor 124, a RF/IQ buffer 126, a user input module 130, a signal processor 132, an image buffer 136, a display system 134, and an archive 138.

The transmitter 102 may comprise suitable logic, circuitry, interfaces and/or code that may be operable to drive one or more ultrasound patch probes 104a, 104b. The ultrasound patch probe(s) 104a, 104b may comprise a one dimensional (1D, 1,25D, 1,5D or 1,75D) array or two dimensional (2D) array of piezoelectric elements. The ultrasound probe(s) 104a, 104b may each comprise a group of transmit transducer elements 106a, 106b and a group of receive transducer elements 108a, 108b, that normally constitute the same elements. In various embodiments, an ultrasound operator may attach ultrasound patch probes 104a, 104b to different patients and/or different patient anatomy using removable and/or interchangeable patch probe bracket(s) 200a, 200b that each has a different ultrasound acquisition angle as described below in connection with FIGS. 2-8. The ultrasound operator may achieve a desired angle of insonation by selecting a patch probe bracket 200a, 200b having an appropriate corresponding ultrasound acquisition angle. Although certain embodiments may illustrate and/or describe two ultrasound patch probes 104a, 104b, for example, unless so claimed, the scope of various aspects of the present disclosure should not be limited to using two ultrasound patch probes 104a, 104b and may additionally and/or alternatively be applicable to any suitable number of ultrasound patch probes 104a, 104b connected to the ultrasound system 100. For example, certain embodiments provide more or less than the two ultrasound patch probes 104a, 104b illustrated in FIG. 1. In various embodiments, with respect to the array(s) of transducer elements 106a, 106b, 108a, 108b in patch probes 104a, 104b, a variety of different geometries and configuration may be used and the transducer elements 106a, 106b, 108a, 108b may be provided as part of, for example, different types of ultrasound patch probes. In certain embodiments, one or more of the transducer elements 106a, 106b, 108a, 108b may be configured having the same geometry, for example, the same size or configuration and may be part of the same type of ultrasound patch probe. In an exemplary embodiment, the ultrasound patch probe(s) 104a, 104b may be configured to communicate with transmitter 102 and receiver 118 via wired 128 and/or wireless communication. For example, the ultrasound patch probe(s) 104a, 104b may be configured to transmit and receive signals using near field communication (NFC), Bluetooth, Wi-Fi, or any suitable wireless technology.

The transmit beamformer 110 may comprise suitable logic, circuitry, interfaces and/or code that may be operable to control the transmitter 102 which, through a transmit sub-aperture beamformer 114a, 114b, drives the group of transmit transducer elements 106a, 106b to emit ultrasonic transmit signals into a region of interest (e.g., human, animal, underground cavity, physical structure and the like).

The transmitted ultrasonic signals may be back-scattered from structures in the object of interest, like blood cells or tissue, to produce echoes. The echoes are received by the receive transducer elements 108a, 108b. The group of receive transducer elements 108a, 108b in each of the ultrasound patch probes 104a, 104b may be operable to convert the received echoes into analog signals, undergo sub-aperture beamforming by a receive sub-aperture beamformer 116a, 116b and are then communicated to a receiver 118.

The multiplexer 112 may comprise suitable logic, circuitry, interfaces and/or code that may be operable to control which of the one or more transmit transducer elements 106a, 106b and/or ultrasound patch probes 104a, 104b is driven, including the specific elements within a particular array of transmit transducer elements 106a, 106b. The multiplexer 112 may comprise suitable logic, circuitry, interfaces and/or code that may be operable to multiplex the echoes received from the receive transducer elements 108a, 108b via the receive sub-aperture beamformers 116a, 116b when using more than one ultrasound patch probe 104a, 104b and corresponding array of receive transducer elements 108a, 108b. In various embodiments, the multiplexer 112 and other switching circuitry may be provided in the housing of the ultrasound patch probe 104a, 104b and/or the housing of the ultrasound system 100.

The receiver 118 may comprise suitable logic, circuitry, interfaces and/or code that may be operable to receive and demodulate the signals from the receive sub-aperture beamformer(s) 116a, 116b via the multiplexer 112. The demodulated analog signals may be communicated to one or more of the plurality of A/D converters 122. The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the disclosure is not limited in this regard. Accordingly, in some embodiments, the plurality of A/D converters 122 may be integrated within the receiver 118.

The receive beamformer 120 may comprise suitable logic, circuitry, interfaces and/or code that may be operable to perform digital beamforming processing on the signals received from the plurality of A/D converters 122. The resulting processed information may be converted back to corresponding RF signals. The corresponding output RF signals that are output from the receive beamformer 120 may be communicated to the RF processor 124. In accordance with some embodiments, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module may be utilized to input patient data, image acquisition and scan parameters, image viewing parameters, settings, configuration parameters, change scan mode, start and stop scanning, and the like. In an exemplary embodiment, the user input module 130 may be operable to configure, manage and/or control operation of one or more components and/or modules in the ultrasound system 100. In this regard, the user input module 130 may be operable to configure, manage and/or control operation of transmitter 102, the ultrasound patch probe(s) 104a, 104b, the transmit beamformer 110, the receiver 118, the receive beamformer 120, the A/D converters 122, the RF processor 124, the RF/IQ buffer 126, the user input module 130, the signal processor 132, the image buffer 136, and/or the display system 134.

The user input module 130 may include physical control devices provided and/or integrated at the ultrasound system 100. For example, the user input module 130 can include a trackball, mousing device, keyboard, touch screen display, remote control, button, switch, rotary encoder, sliding bar, and/or voice activated input, among other things. The user input module 130 may be integrated with other components, such as the ultrasound patch probe(s) 104a, 104b, display system 134 or control panel, or can be a separate component.

The signal processor 132 may comprise suitable logic, circuitry, interfaces and/or code that may be operable to control operation of the ultrasound system 100 and process the ultrasound scan data (i.e., RF signal data or IQ data pairs) for generating an ultrasound image for presentation on a display system 134. The signal processor 132 is operable to perform one or more processing operations according to a plurality of selectable ultrasound modalities on the acquired ultrasound scan data. In an exemplary embodiment of the disclosure, the signal processor 132 may be operable to perform volume rendering, compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 and/or the archive 138 during a scanning session and processed in less than real-time in a live or off-line operation. The processed image data can be presented at the display system 134, inserted into a report, and/or stored at the archive 138. The archive 138 may be a local archive, a Picture Archiving and Communication System (PACS), or any suitable device for storing images and related information.

The ultrasound system 100 may be operable to continuously acquire ultrasound information at a frame rate that is suitable for the imaging situation in question. Typical frame rates range from 20-70 but may be lower or higher. The acquired ultrasound information may be displayed on the display system 134 at a display-rate that can be the same as the frame rate, or slower or faster. An image buffer 136 is included for storing processed frames of acquired ultrasound information that are not scheduled to be displayed immediately. Preferably, the image buffer 136 is of sufficient capacity to store at least several seconds worth of frames of ultrasound information. The frames of ultrasound information are stored in a manner to facilitate retrieval thereof according to its order or time of acquisition. The image buffer 136 may be embodied as any known data storage medium.

FIGS. 2-6 provide perspective and side views of an exemplary ultrasound patch probe 104 being attached to an exemplary ultrasound patch probe bracket 200 having an ultrasound acquisition angle of approximately 45 degrees, in accordance with various embodiments. FIG. 7 is a perspective view of an exemplary ultrasound patch probe 104 being inserted into an exemplary ultrasound patch probe bracket 200 having an ultrasound acquisition angle of approximately 90 degrees, in accordance with various embodiments. Referring to FIGS. 2-7, the ultrasound patch probe bracket 200 comprises a bracket base 202 and a bracket body 204. The bracket base 202 is operable to support the bracket body 204. The bracket base 202 may include a bottom surface 214 operable to be placed at a desired location against skin of a patient. The bracket base 202 may generally surround a perimeter of the bracket body 204 and define an opening that extends through the bracket base 202 to provide access to a hollow interior portion of the bracket body 204.

The bracket body 204 extends from the bracket base 202 and comprises a bracket probe coupler 206 operable to receive an ultrasound patch probe 104. The bracket body 204 may define a hollow interior portion that extends between the bracket probe coupler 206 and the opening extending through the bracket base 202. The bracket probe coupler 206 opening, the hollow interior portion of the bracket body 204, and the opening extending through the bracket base 202 form a channel through which ultrasound signals are emitted and ultrasound echoes are received by an attached ultrasound patch probe 104. The channel may be packed with an ultrasound gel pad 212 configured to fill the hollow space and press against the transducer surface of an attached ultrasound patch probe 104 and the skin of a patient to provide a conductive medium facilitating ultrasound wave transmission and reception between the patch probe 104 and the skin of the patient. In various embodiments, the ultrasound gel pad 212 may be configured to extend into and/or slightly beyond the openings in the bracket base 202 and bracket probe coupler 206 to provide a press fit against the surface of the transducer and the surface of the skin when the ultrasound patch probe 104 is attached to the bracket 200 and the bracket is secured to the skin of the patient.

The bracket body 204 may be arranged to position the bracket probe coupler 206 in such a way that ultrasound signals are transmitted from an ultrasound patch probe 104 at a particular, pre-defined ultrasound acquisition angle. The ultrasound acquisition angle is defined as the angle between the ultrasound beams transmitted from the ultrasound patch probe 104 through the opening in the bracket base 202 and the lengthwise axis of the bracket base 202 (i.e., the horizontal plane of the bracket base 202 in FIGS. 4-7). In various embodiments, the ultrasound acquisition angle may be substantially the same as an angle of insonation when the target reflector is substantially parallel to the lengthwise axis of the bracket base 202. In an exemplary embodiment, a set of ultrasound patch probe brackets 200, each having a different ultrasound acquisition angle, may be provided such that the an ultrasound operator may select one of the brackets 200 having an ultrasound acquisition angle corresponding to a desired angle of insonation for use with the ultrasound patch probe 104. The ultrasound patch probe brackets 200 each having the different ultrasound acquisition angle may be interchangeable and detachably coupleable to the ultrasound patch probe 104 such that the probe 104 can be used with any of the brackets 200 at a variety of different angles. For example, a set of ultrasound patch probe brackets 200 may include brackets having acquisition angles of 15 degrees, 30 degrees, 45 degrees, 60 degrees, and 90 degrees, or any suitable angle above 0 degrees and up to 90 degrees. For purposes of the present disclosure, the term "approximately 45 degrees" is defined as a range of 30 degrees to 60 degrees.

The bracket probe coupler 206 may define a slot as illustrated in FIG. 7 or cavity as illustrated in FIGS. 2-6 that the ultrasound patch probe 104 may snap and/or slide into. Referring to the exemplary embodiment shown in FIGS. 2-6, the bracket probe coupler 206 may include bracket probe coupler cable clearings 208 at opposite ends of the bracket probe coupler 206 for cable management purposes. For example, the bracket probe coupler cable clearings 208 of the bracket probe coupler 206 allows the ultrasound patch probe 104 having a cable 128 to be attached to the bracket probe coupler 206 in a first direction or a second opposite direction with the cable 128 passing through the respective clearing 208. Referring to FIG. 7, although the ultrasound probe bracket 200 is shown having one bracket probe coupler 206 slot access opening, for example, unless so claimed, the scope of various aspects of the present disclosure should not be limited to one bracket probe coupler 206 slot access opening and may additionally and/or alternatively include multiple bracket probe coupler 206 slot access openings. For example, certain embodiments provide access to the bracket probe coupler 206 slot from opposite sides of the bracket 200 for cable management purposes.

Referring again to FIGS. 2-6, the bracket probe coupler 206 may include a detachment mechanism 210. For example, the detachment mechanism 210 may be an opening to provide access to a portion of the ultrasound patch probe 104 so that the probe 104 may be pivoted out of the bracket probe coupler 206 to remove the probe 104 from the bracket 200. Other examples of detachment mechanisms 210 may include a pull tab, button-activated extension mechanism, or the like for creating separation between the ultrasound patch probe 104 and the bracket probe coupler 206 so that the probe 104 may be removed from the bracket 200.

Figure 2:
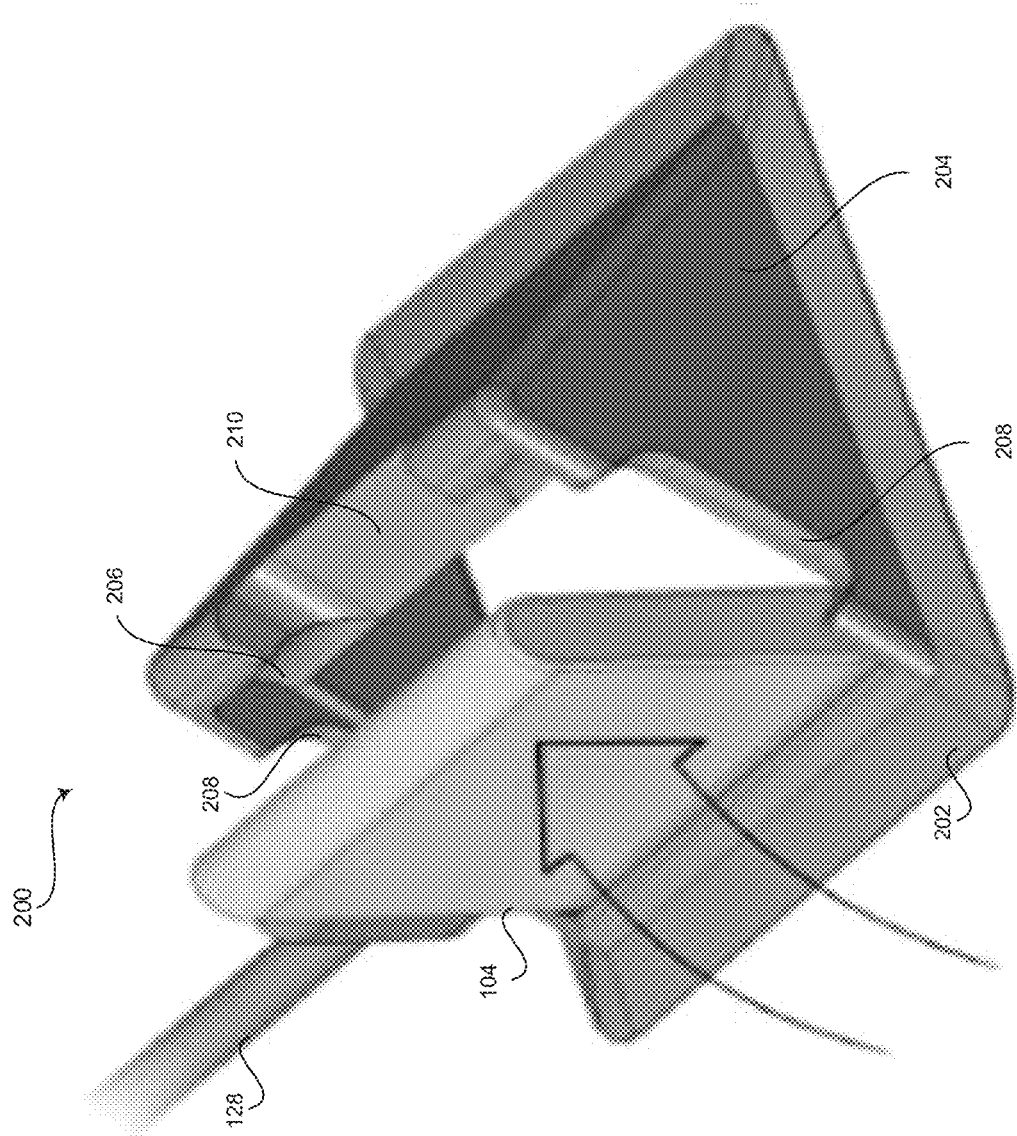
FIG. 2 is a perspective view of an exemplary ultrasound patch probe being attached to an exemplary ultrasound patch probe bracket having an ultrasound acquisition angle of approximately 45 degrees, in accordance with various embodiments.
Figure 3:
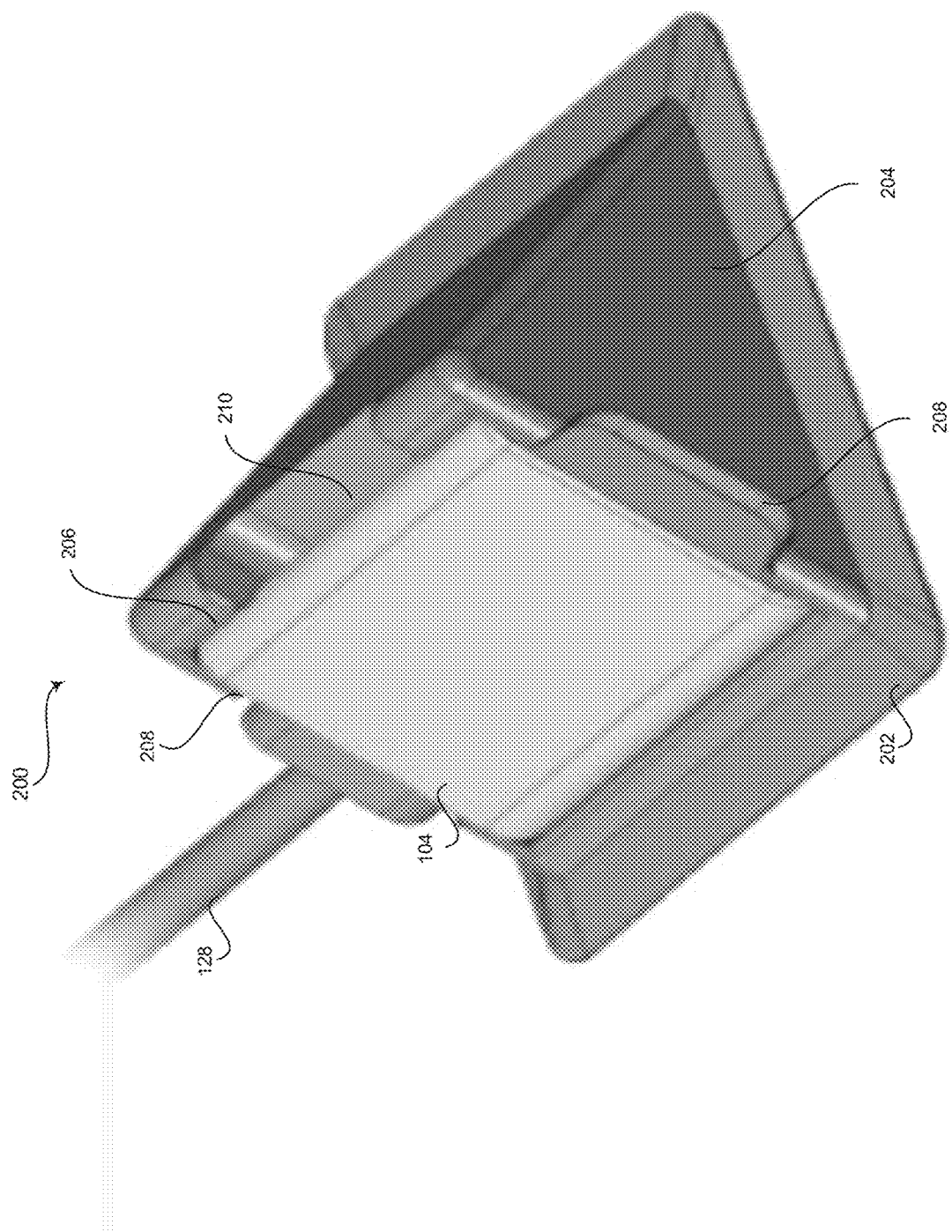
FIG. 3 is a perspective view of an exemplary ultrasound patch probe attached to an exemplary ultrasound patch probe bracket having an ultrasound acquisition angle of approximately 45 degrees, in accordance with various embodiments.
Figure 4:
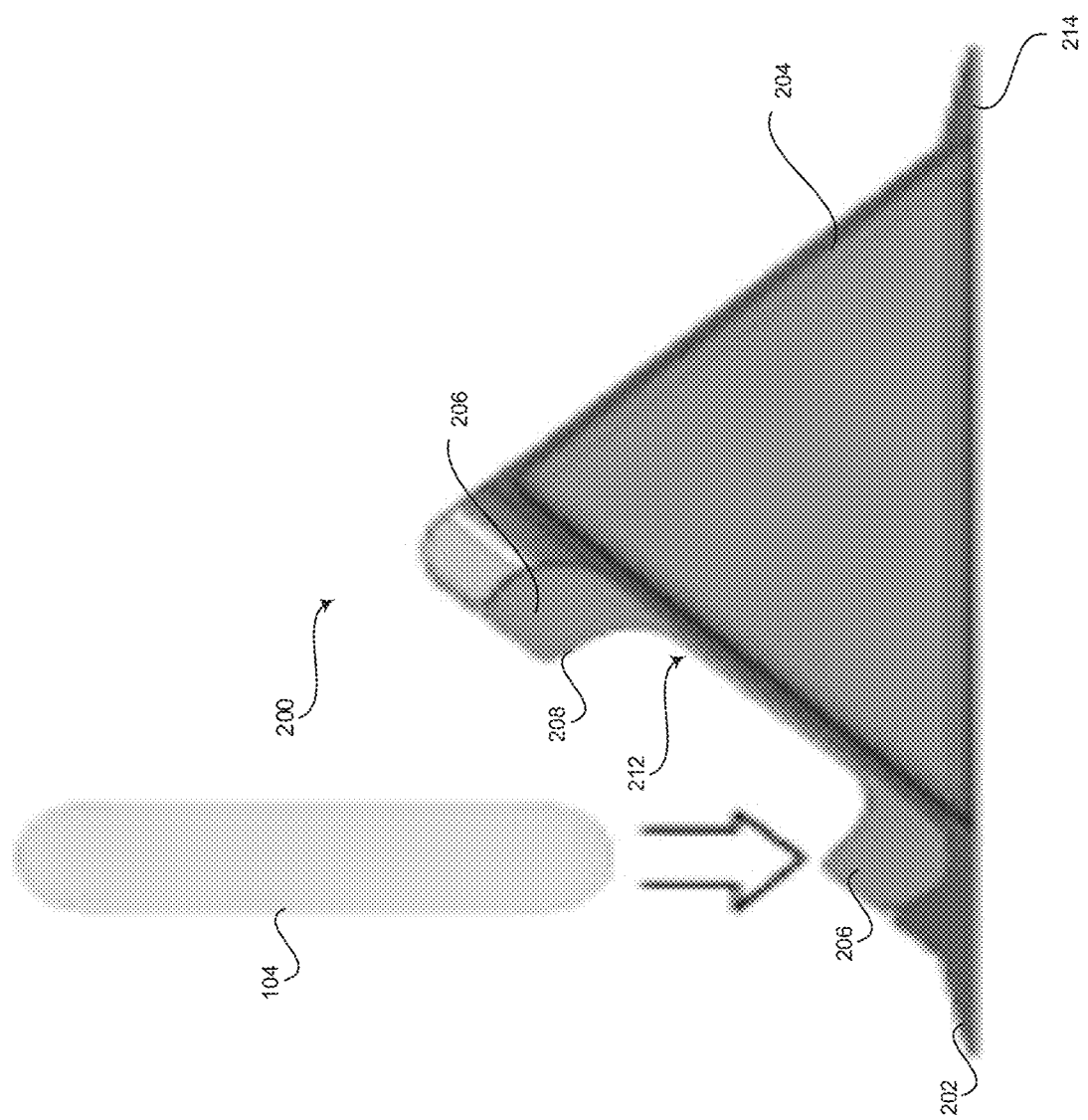
FIG. 4 is a side view of an exemplary ultrasound patch probe being inserted into an exemplary snap-in attachment mechanism of an exemplary ultrasound patch probe bracket having an ultrasound acquisition angle of approximately 45 degrees, in accordance with various embodiments.
Figure 5:
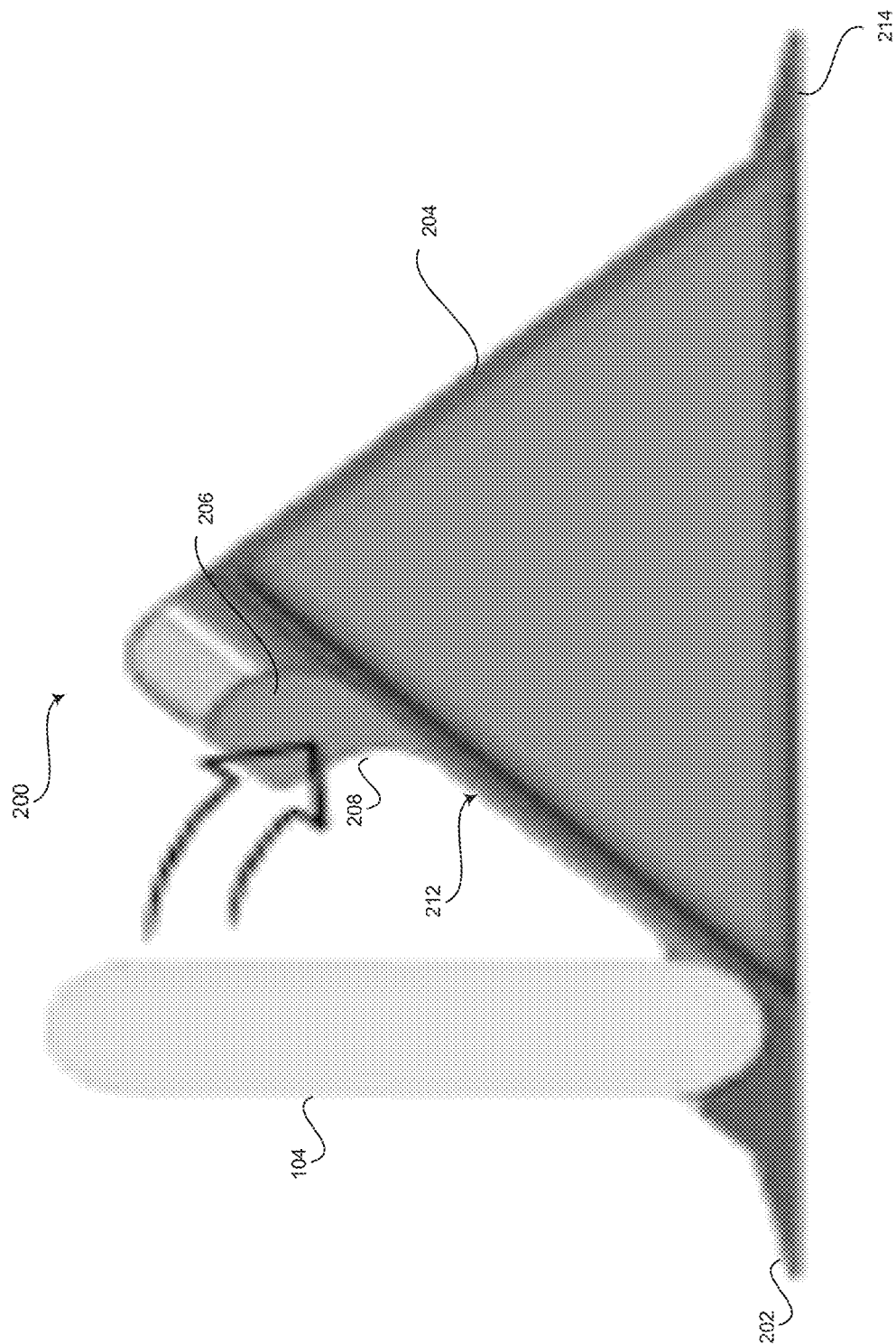
FIG. 5 is a side view of an exemplary ultrasound patch probe being rotated within an exemplary snap-in attachment mechanism of an exemplary ultrasound patch probe bracket having an ultrasound acquisition angle of approximately 45 degrees, in accordance with various embodiments.
Figure 6:
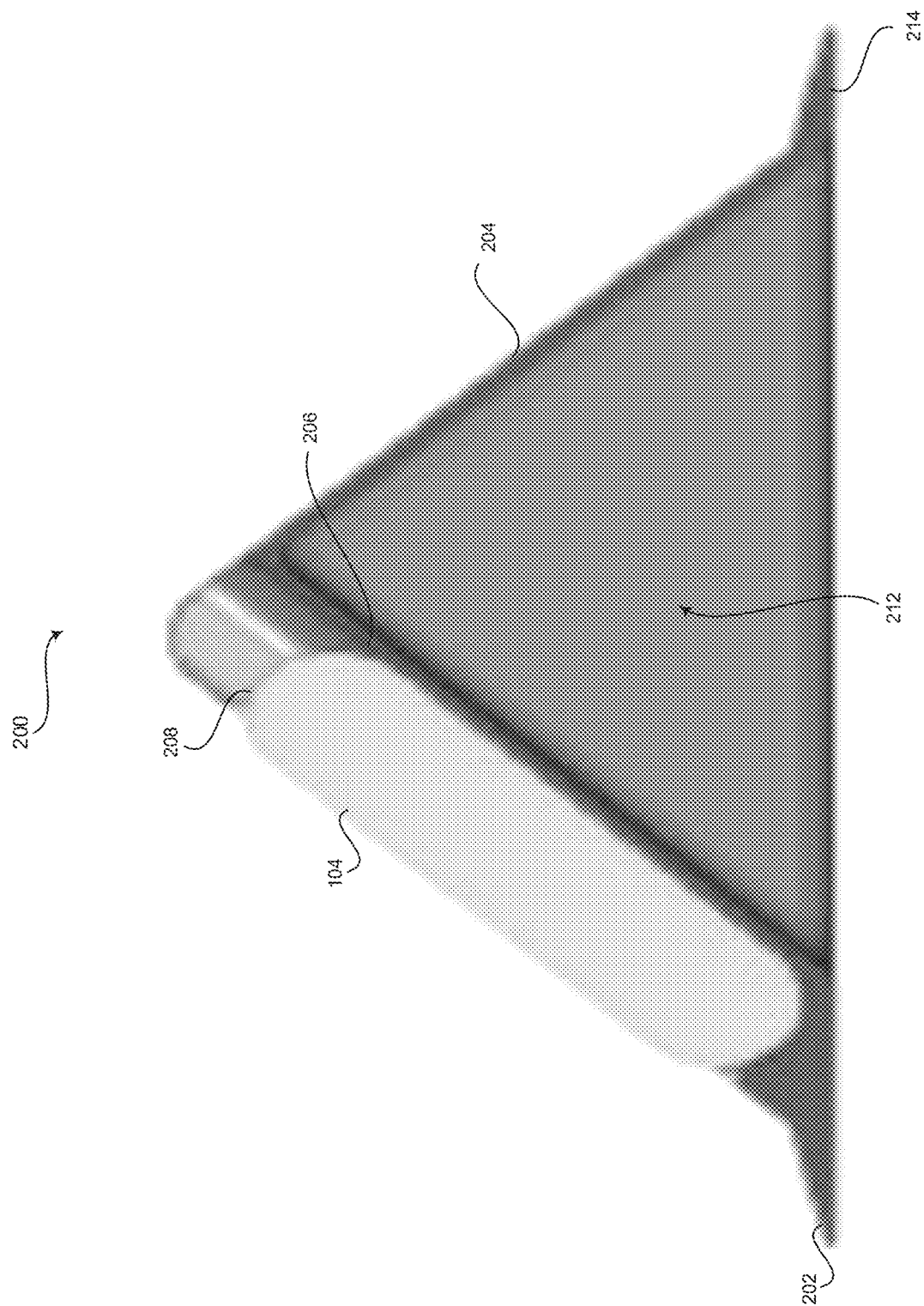
FIG. 6 is a side view of an exemplary ultrasound patch probe attached into an exemplary snap-in attachment mechanism of an exemplary ultrasound patch probe bracket having an ultrasound acquisition angle of approximately 45 degrees, in accordance with various embodiments.
Figure 7:
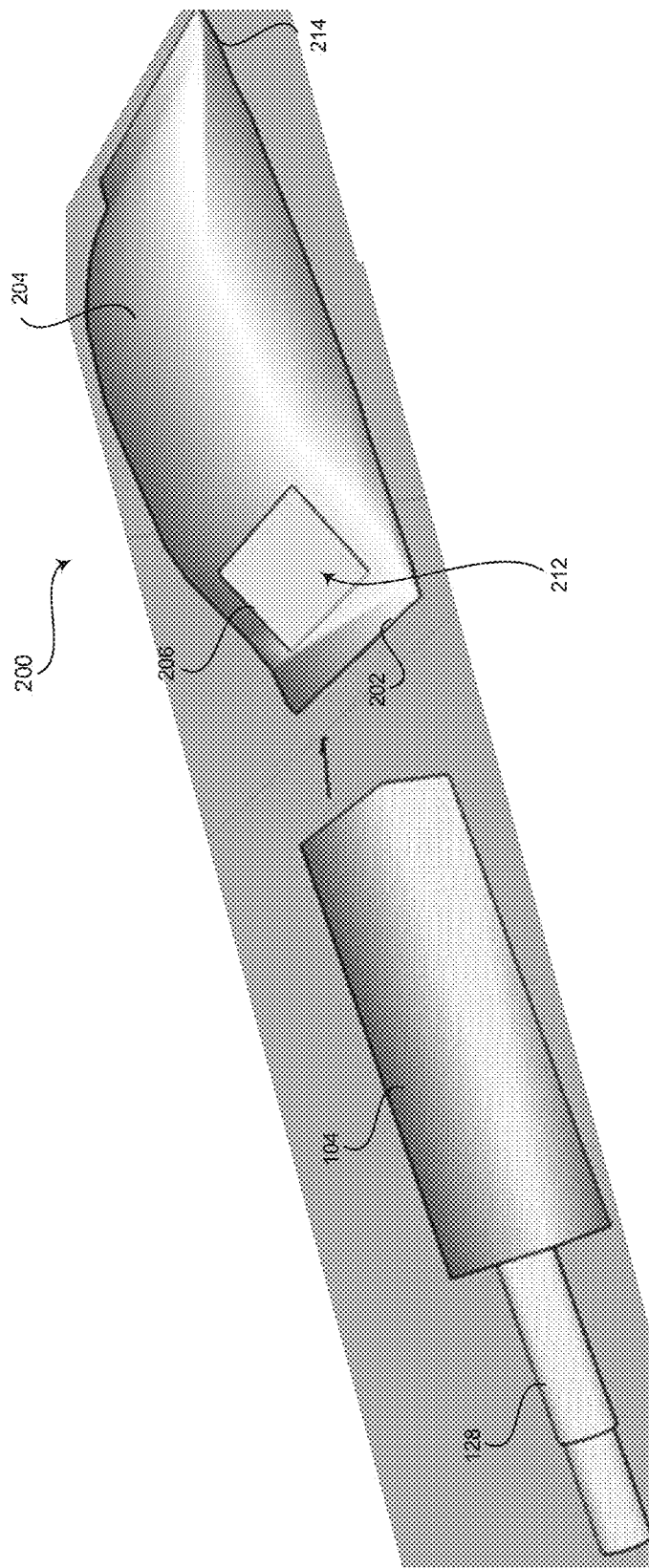
FIG. 7 is a perspective view of an exemplary ultrasound patch probe being inserted into an exemplary ultrasound patch probe bracket having an ultrasound acquisition angle of approximately 90 degrees, in accordance with various embodiments.

Still referring to FIGS. 2-6, an ultrasound patch probe 104 is shown being snapped into an exemplary embodiment of a bracket probe coupler 206 of an ultrasound patch probe bracket 200. For example, a first side of the ultrasound patch probe 104 may be inserted into a first side of the bracket probe coupler 206 as illustrated in FIG. 4. The ultrasound patch probe 104 may pivot about the inserted side to snap the opposite side of the probe 104 into a second, opposite side of the bracket probe coupler 206 as illustrated in FIGS. 2 and 5. The bracket probe coupler 206 may include clearings 208 so that the cable 128 of the ultrasound patch probe 104 may extend out of the ultrasound patch probe bracket 200 via the clearings 208 in either of the two opposite directions. The ultrasound patch probe 104 fully attached within the bracket probe coupler 206 of the ultrasound patch probe bracket 200 is illustrated in FIGS. 3 and 6. In various embodiments, the ultrasound patch probe 104 may be removed from the bracket probe coupler 206 by pivoting the probe 104 in an opposite direction. The detachment mechanism 210 is provided to allow easy access to the probe 104 so the probe 104 may be rotated to unsnap and remove the probe 104 from the bracket probe coupler 206.

Figure 8:
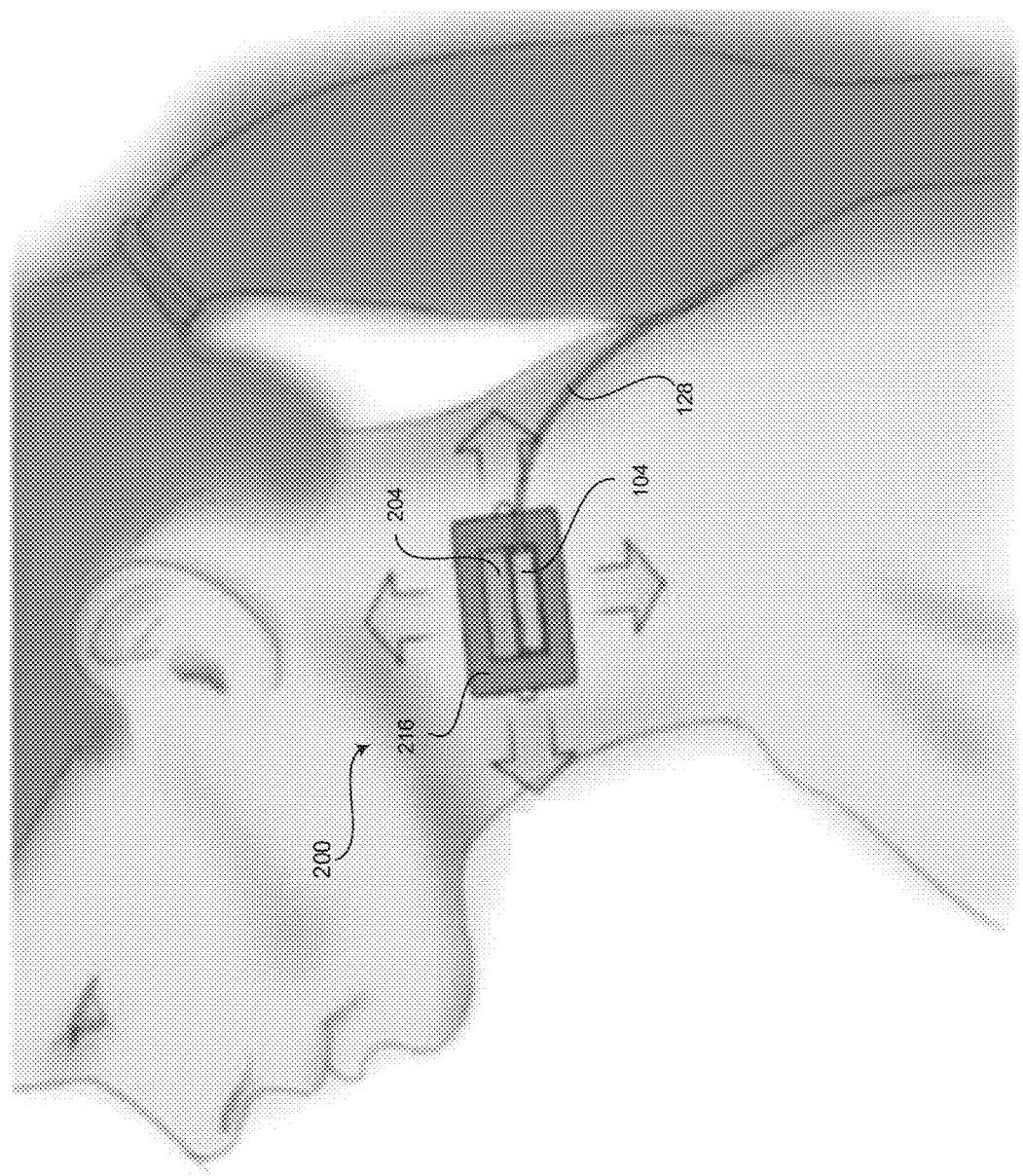
FIG. 8 is a perspective view of an exemplary ultrasound patch probe attached to an exemplary ultrasound patch probe bracket affixed to skin of a patient, in accordance with various embodiments.

FIG. 8 is a perspective view of an exemplary ultrasound patch probe 104 attached to an exemplary ultrasound patch probe bracket 200 affixed to skin of a patient, in accordance with various embodiments. Referring to FIG. 8, an ultrasound patch probe 104 having a cable 128 for wired connection with an ultrasound system 100 is attached to an ultrasound patch probe bracket 200 having a bracket base 202, bracket body 204, and adhesive patch 216. The adhesive patch 216 may be a peel and stick patch, or any suitable adhesive patch, attached to and extending beyond the bracket base 202. The adhesive patch 216 may attach both to the bracket base 202 and the skin of the patient so that the bottom surface 214 of the bracket base 202 is firmly secured at a desired position against the skin of the patient. Additionally and/or alternatively, an adhesive may be applied to the bottom surface 214 of the bracket base 202 so that the bottom surface 214 affixes to the skin of the patient.

Figure 9:
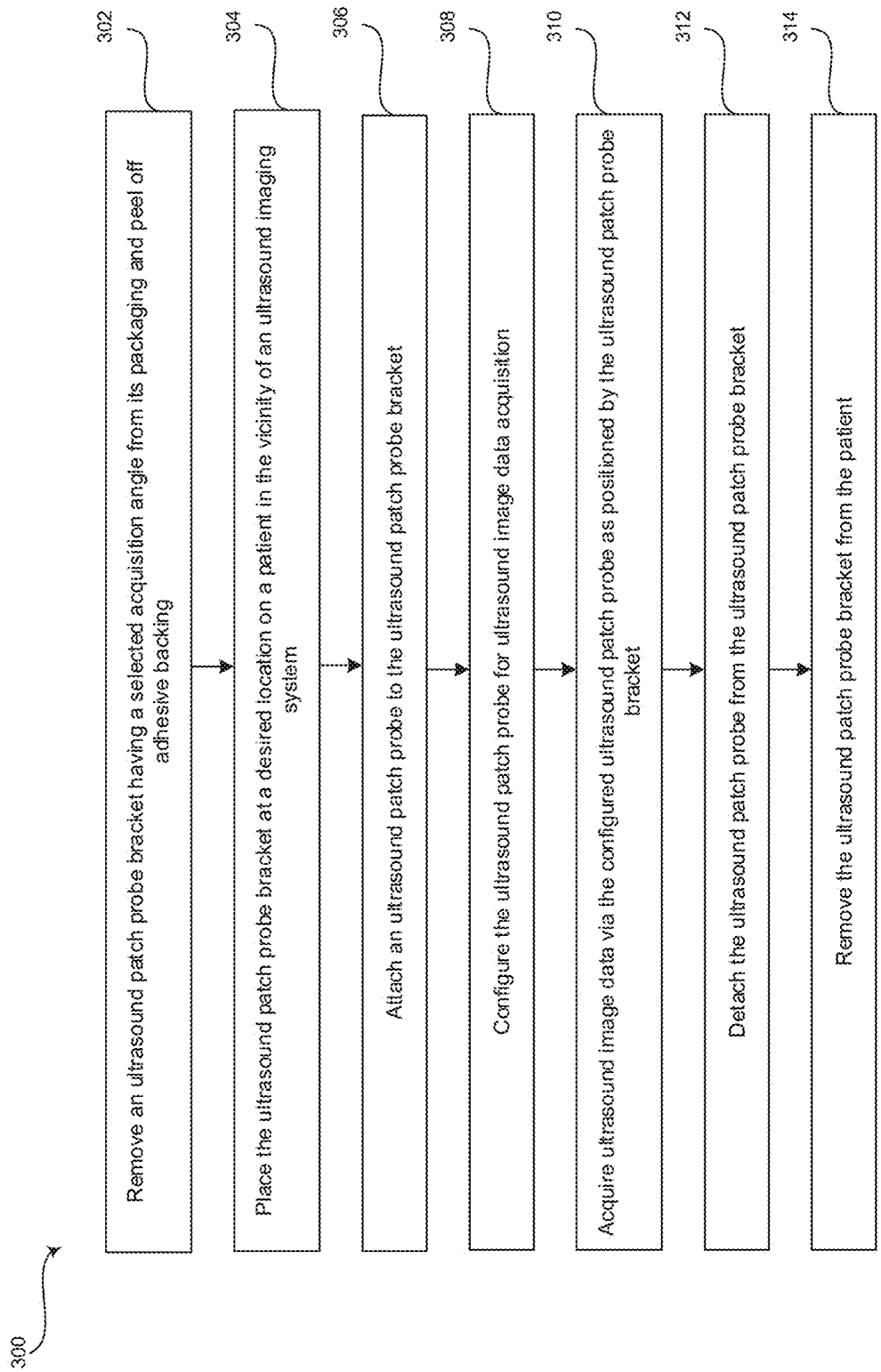
FIG. 9 is a flow chart illustrating exemplary steps that may be utilized for using an ultrasound patch probe with an interchangeable patch probe bracket to acquire ultrasound image data at a selected angle of insonation, in accordance with various embodiments.

FIG. 9 is a flow chart illustrating exemplary steps 302-314 that may be utilized for using an ultrasound patch probe 104, 104a, 104b with an interchangeable patch probe bracket 200, 200a, 200b to acquire ultrasound image data at a selected angle of insonation, in accordance with various embodiments. Referring to FIG. 9, there is shown a flow chart 300 comprising exemplary steps 302 through 314. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, an ultrasound operator may remove an ultrasound patch probe bracket 200, 200a, 200b having a selected ultrasound acquisition angle from its packaging and peel off adhesive 216 backing. For example, ultrasound patch probe brackets 200, 200a, 200b having a variety of ultrasound acquisition angles greater than 0 degrees and up to 90 degrees may be individually packaged. The ultrasound operator may select the bracket 200, 200a, 200b based on a desired ultrasound acquisition angle. As an example, an ultrasound operator may desire to perform a blood flow velocity measurement with an ultrasound patch probe 104 operating in a Doppler mode. If the ultrasound operator wants a 60 degree angle of insonation and expects the target vessel to be substantially parallel to the skin of the patient, the operator may select a bracket 200, 200a, 200b having a 60 degree ultrasound acquisition angle. The ultrasound operator may select a bracket 200, 200a, 200b having a different angle if the vessel is angled with respect to the skin of the patient and/or if a different angle of insonation is desired. The ultrasound patch probe brackets 200, 200a, 200b may be provided at a variety of different increments, such as 2.5 degree increments, 5 degree increments, 10 degree increments, 15 degree increments, and the like. The size of the increments may vary depending on the range of ultrasound acquisition angles. For example, a larger number of smaller spaced increments may be available in a range of 30 degrees to 60 degrees with fewer options more spaced apart below 30 degrees and above 60 degrees. The set of ultrasound patch probe brackets 200, 200a, 200b provide a variety of options for assisting an ultrasound operator to interchangeably select the ultrasound acquisition angle to enhance the image data acquired with ultrasound patch probes 104, 104a, 104b. In various embodiments, each of the brackets may be individually packaged, such as in a blister pack or any suitable packaging, to maintain sterilization. In certain embodiments, the brackets 200, 200a, 200b may include an adhesive backing that may be peeled off to access the adhesive material. Additionally and/or alternatively, an adhesive may be separately applied to the skin of the patient and/or the bracket 200, 200a, 200b after the bracket is removed from the packaging.

At step 304, the ultrasound operator may place the ultrasound patch probe bracket 200, 200a, 200b at a desired location on a patient in the vicinity of an ultrasound imaging system 100. For example, a bracket may be affixed at a location on the skin of a patient corresponding to a particular patient anatomy, such as the left common carotid artery, the posterior side of the left lung, or any suitable patient anatomy, for which prolonged ultrasound monitoring is desired. The adhesive attached and/or applied to the bracket 200, 200a, 200b may securely but detachably couple the bracket 200, 200a, 200b to the skin of the patient at the selected position and orientation.

At step 306, the ultrasound operator may attach an ultrasound patch probe 104, 104a, 104b to the ultrasound patch probe bracket 200, 200a, 200b. For example, the operator may insert a first side of the ultrasound patch probe 104 into a first side of the bracket probe coupler 206 as illustrated in FIG. 4. The ultrasound patch probe 104 may be rotated to snap the opposite side of the probe 104 into a second, opposite side of the bracket probe coupler 206 as illustrated in FIGS. 2 and 5 so that the ultrasound patch probe 104 is detachably coupled within the bracket probe coupler 206 as illustrated in FIGS. 3 and 6. As another example, the ultrasound patch probe 104 may be inserted into an ultrasound patch probe bracket 200 slot as illustrated in FIG. 7.

At step 308, the ultrasound system 100 may configure the ultrasound patch probe 104, 104a, 104b for ultrasound image acquisition. For example, a signal processor 132 of an ultrasound imaging system 100 may detect the presence of the ultrasound patch probe 104, 104a, 104b attempting to connect with the ultrasound imaging system 100 via wired 128 or wireless communications. As an example, an ultrasound imaging system operator may plug an ultrasound patch probe 104, 104a, 104b into the ultrasound imaging system 100 and/or the ultrasound patch probe 104, 104a, 104b may include a transceiver operable to transmit signals to and receive signals from a transceiver of the ultrasound imaging system 100. The signals received at the transceiver of the ultrasound imaging system 100 from the ultrasound patch probe 104, 104a, 104b may be provided to the signal processor 132 of the ultrasound imaging system 100. The signal processor 132 may analyze information provided in the received signal, such as identification information and the type of ultrasound patch probe, to determine whether an authorized ultrasound patch probe 104, 104a, 104b has been detected. The signal processor 132 may configure the detected ultrasound probe 104a, 104b based on, for example, stored settings associated with the particular examination type, ultrasound patch probe 104a, 104b type, and/or instructions provided by an operator via a user input module 130 of the ultrasound imaging system 100. In various embodiments, the signal processor 132 may provide a configuration dialog user interface to allow the ultrasound operator to provide text, button selections, drop-down menu selections, and/or the like to configure the detected ultrasound patch probe 104, 104a, 104b. For example, the ultrasound operator may configure the ultrasound patch probe 104, 104a, 104b by setting parameters executable by the ultrasound imaging system 100 to acquire ultrasound data via the ultrasound patch probe 104, 104a, 104b.

At step 310, the ultrasound imaging system 100 may continuously acquire ultrasound image data from the configured ultrasound patch probe 104, 104a, 104b at positioned by the ultrasound patch probe bracket 200, 200a, 200b. For example, the ultrasound patch probe 104a, 104b, under the control of the ultrasound imaging system 100, may continuously acquire ultrasound image data at the selected ultrasound acquisition angle provided by the ultrasound patch probe bracket 200, 200a, 200b. The ultrasound patch probe bracket 200 may comprise a gel pad that presses against the transducer surface of the ultrasound patch probe 104, 104a, 104b and the skin of the patient when the ultrasound patch probe bracket 200, 200a, 200b is affixed to the skin of the patient and the probe 104, 104a, 104b is detachably coupled to the bracket 200, 200a, 200b to provide a conductive medium for transmission and reception of ultrasound waves. The data flow from the ultrasound patch probe 104a, 104b may be received and processed at the signal processor 132 for presentation at a display system 134, storage at an archive 138 or any suitable data storage medium, and/or the like.

At step 312, the ultrasound patch probe 104, 104a, 104b may be detached from the ultrasound patch probe bracket 200, 200a, 200b. For example, the ultrasound patch probe 104, 104a, 104b may be removed from a bracket probe coupler 206 of the bracket 200, 200a, 200b by pivoting or sliding the probe 104, 104a, 104b away from the bracket probe coupler 206. The ultrasound patch probe bracket 200, 200a, 200b may include a detachment mechanism 210 to provide access to the probe 104, 104a, 104b so the probe may be rotated to unsnap and remove the probe 104, 104a, 104b from the bracket probe coupler 206. In a representative embodiment, the ultrasound patch probe 104, 104a, 104b may be subsequently reused with another ultrasound patch probe bracket 200a, 200a, 200b at a same or different location on a same or different patient. In various embodiments, the probe 104, 104a, 104b may be removed from the bracket 200, 200a, 200b after the ultrasound operator provides an instruction to the ultrasound imaging system 100 that the ultrasound image acquisition of step 310 is complete. For example, an ultrasound imaging system operator may disconnect the probe 104a, 104b from the ultrasound imaging system 100 by providing an instruction provided to the ultrasound imaging system 100 via the user input module 130, powering off the ultrasound probe 104a, 104b, and/or breaking an electrical connection between the ultrasound probe 104a, 104b and the ultrasound imaging system 100, among other things.

At step 314, the ultrasound patch probe bracket 200, 200a, 200b may be removed from the patient. For example, the ultrasound patch probe bracket 200, 200a, 200b may be removed by pulling the bracket 200, 200a, 200b from the skin of the patient. In various embodiments, warm water, baby oil, rubbing alcohol or the like may be applied to the adhesive patch 216 or any suitable adhesive to assist removing the bracket 200, 200a, 200b and/or remaining adhesive residue left on the skin of the patient.

Aspects of the present disclosure provide a method 300 and system 100 for enhancing ultrasound image acquisition using ultrasound patch probes 104a, 104b with interchangeable brackets 200a, 200b having a variety of acquisition angles. In accordance with various embodiments, the system comprises a plurality of ultrasound patch probe brackets 200, 200a, 200b. Each of the ultrasound patch probe brackets 200, 200a, 200b comprises a bracket body 204 having a bracket probe coupler 206 and a hollow interior portion. The bracket probe coupler 206 is operable to receive an ultrasound patch probe 104, 104a, 104b at a pre-defined ultrasound acquisition angle. The bracket probe coupler 206 defines a probe opening to provide the ultrasound patch probe 104, 104a, 104b access to the hollow interior portion of the bracket body 204. The bracket probe coupler 206 of each of the ultrasound patch probe brackets 200, 200a, 200b is arranged to receive the ultrasound patch probe 104, 104a, 104b at a different pre-defined ultrasound acquisition angle. Each of the ultrasound patch probe brackets 200, 200a, 200b comprises a bracket base 202 surrounding a perimeter of the bracket body 204 and defining a bracket opening that extends through the bracket base 202 to provide access to the hollow interior portion of the bracket body 204. The bracket base 202 comprises a bottom surface 214 operable to be secured against skin of a patient. The ultrasound patch probe 104, 104a, 104b is communicatively coupled to an ultrasound imaging system 100 and detachably coupleable to the bracket probe coupler 206 of any selected one of the plurality of ultrasound patch probe brackets 200, 200a, 200b. The ultrasound patch probe 104, 104a, 104b comprises a transducer surface. The probe opening, the hollow interior portion, and the bracket opening form an ultrasound acquisition channel for the transmission and reception of ultrasound signals between the transducer surface of the ultrasound patch probe 104, 104a, 104b and the skin of the patient if the ultrasound patch probe 104, 104a, 104b is detachably coupled to the bracket probe coupler 206 and the bottom surface 214 is secured against the skin of the patient.

In various embodiments, the system comprises an ultrasound gel pad 212 disposed within the hollow interior portion of the bracket body 204. In certain embodiments, the ultrasound gel pad 212 at least partially extends into one or both of the probe opening and the bracket opening. In an exemplary embodiment, the bracket probe coupler 206 comprises a first bracket probe cable clearing 208 at a first end of the bracket probe coupler 206 and a second bracket probe clearing 208 at a second opposite end of the bracket probe coupler 206. In a representative embodiment, the ultrasound patch probe 104, 104a, 104b is communicatively coupled to the ultrasound imaging system 100 by a cable 128. In various embodiments, the cable 128 passes through the first bracket probe clearing 208 if the ultrasound patch probe 104, 104a, 104b is detachably coupled to the bracket probe coupler 206 in a first direction. The cable 128 passes through the second bracket probe clearing 208 if the ultrasound patch probe 104, 104a, 104b is detachably coupled to the bracket probe coupler 206 in a second opposite direction.

In certain embodiments, the bracket body 204 comprises a detachment mechanism 210 having an opening to provide access to a portion of the ultrasound patch probe 104, 104a, 104b for removal of the ultrasound patch probe 104, 104a, 104b from the bracket probe coupler 206. In an exemplary embodiment, the selected one of the plurality of ultrasound patch probe brackets 200, 200a, 200b includes a pre-defined ultrasound acquisition angle of approximately 45 degrees (i.e., 30-60 degrees). In a representative embodiment, the ultrasound patch probe 104, 104a, 104b is detachably coupled to the bracket probe coupler 206 by inserting a first side of the ultrasound patch probe 104, 104a, 104b into a first side of the bracket probe coupler 206. The second opposite side of the ultrasound patch probe 104, 104a, 104b is pivoted about the inserted first side of the ultrasound patch probe 104, 104a, 104b into a second, opposite side of the bracket probe coupler 206. In various embodiments, the ultrasound patch probe 104, 104a, 104b is detachably coupled to the bracket probe coupler 206 by sliding the ultrasound patch probe 104, 104a, 104b into a slot defined by the bracket probe coupler 206. In certain embodiments, the system comprises an adhesive patch 216 attached to the bracket base 202 and configured to detachably couple with the skin of the patient.

Various embodiments provide an ultrasound patch probe bracket 200, 200a, 200b comprising a bracket body 204 having a bracket probe coupler 206 and a hollow interior portion. The bracket probe coupler 206 is operable to receive an ultrasound patch probe 104, 104a, 104b at a pre-defined ultrasound acquisition angle. The bracket probe coupler 206 defines a probe opening to provide the ultrasound patch probe 104, 104a, 104b access to the hollow interior portion of the bracket body 204. The ultrasound patch probe bracket 200, 200a, 200b comprises a bracket base 202 surrounding a perimeter of the bracket body 204 and defining a bracket opening that extends through the bracket base 202 to provide access to the hollow interior portion of the bracket body 204.

The bracket base 202 comprises a bottom surface 214 operable to be secured against skin of a patient. The probe opening, the hollow interior portion, and the bracket opening form an ultrasound acquisition channel for the transmission and reception of ultrasound signals between a transducer surface of the ultrasound patch probe 104, 104a, 104b and the skin of the patient if the ultrasound patch probe 104, 104a, 104b is detachably coupled to the bracket probe coupler 206 and the bottom surface 214 is secured against the skin of the patient.

In an exemplary embodiment, the ultrasound patch probe bracket 200, 200a, 200b comprises an ultrasound gel pad 212 disposed within the hollow interior portion of the bracket body 204. In a representative embodiment, the ultrasound gel pad 212 at least partially extends into one or both of the probe opening and the bracket opening. In various embodiments, the bracket probe coupler 206 comprises a first bracket probe cable clearing 208 at a first end of the bracket probe coupler 206 and a second bracket probe clearing 208 at a second opposite end of the bracket probe coupler 206. In certain embodiments, the bracket body 204 comprises a detachment mechanism 210 having an opening to provide access to a portion of the ultrasound patch probe 104, 104a, 104b for removal of the ultrasound patch probe 104, 104a, 104b from the bracket probe coupler 206.

In a representative embodiment, the selected one of the plurality of ultrasound patch probe brackets 200, 200a, 200b includes a pre-defined ultrasound acquisition angle of approximately 45 degrees (i.e., 30-60 degrees). In an exemplary embodiment, the ultrasound patch probe bracket 200, 200a, 200b comprises an adhesive patch 216 attached to the bracket base 202 and configured to detachably couple with the skin of the patient. In various embodiments, the bracket probe coupler 206 defines a slot configured to slideably receive the ultrasound patch probe 104, 104a, 104b. In certain embodiments, the bracket probe coupler 206 comprises a first side configured to receive an insertion of a first side of the ultrasound patch probe 104, 104a, 104b. The bracket probe coupler 206 comprises a second side, opposite the first side, configured to receive a second opposite side of the ultrasound patch probe 104, 104a, 104b.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhancing ultrasound image acquisition using ultrasound patch probes 104a, 104b with interchangeable brackets 200a, 200b having a variety of acquisition angles.

Accordingly, various embodiments may be realized in hardware, software, or a combination of hardware and software. Various embodiments may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While various embodiments have been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A system, comprising:
    a plurality of ultrasound patch probe brackets, wherein each of the ultrasound patch probe brackets comprises:
        a bracket body having a bracket probe coupler and a hollow interior portion, the bracket probe coupler provided at a single, pre-defined angle, the bracket probe coupler operable to receive an ultrasound patch probe at a single, pre-defined ultrasound acquisition angle based on the single, pre-defined angle of the bracket probe coupler, wherein the bracket probe coupler defines a probe opening to provide the ultrasound patch probe access to the hollow interior portion of the bracket body, and wherein the bracket probe coupler of each of the ultrasound patch probe brackets is configured to receive the ultrasound patch probe at a different single, pre-defined ultrasound acquisition angle, and
        a bracket base surrounding a perimeter of the bracket body and defining a bracket opening that extends through the bracket base to provide access to the hollow interior portion of the bracket body, the bracket base comprising a bottom surface operable to be secured against skin of a patient; and the ultrasound patch probe communicatively coupled to an ultrasound imaging system and configured to detachably couple within the bracket probe coupler of any selected one of the plurality of ultrasound patch probe brackets, the ultrasound patch probe comprising a transducer surface, wherein the probe opening, the hollow interior portion, and the bracket opening form an ultrasound acquisition channel for the transmission and reception of ultrasound signals between the transducer surface of the ultrasound patch probe and the skin of the patient if the ultrasound patch probe is detachably coupled to the bracket probe coupler and the bottom surface is secured against the skin of the patient.

2. The system of claim 1, comprising an ultrasound gel pad disposed within the hollow interior portion of the bracket body.

3. The system of claim 2, wherein the ultrasound gel pad at least partially extends into one or both of the probe opening and the bracket opening.

4. The system of claim 1, wherein the bracket probe coupler comprises a first bracket probe cable clearing at a first end of the bracket probe coupler and a second bracket probe clearing at a second opposite end of the bracket probe coupler.

5. The system of claim 4, wherein the ultrasound patch probe is communicatively coupled to the ultrasound imaging system by a cable.

6. The system of claim 5, wherein:
the cable passes through the first bracket probe clearing if the ultrasound patch probe is detachably coupled to the bracket probe coupler in a first direction, and
the cable passes through the second bracket probe clearing if the ultrasound patch probe is detachably coupled to the bracket probe coupler in a second opposite direction.

7. The system of claim 1, wherein the bracket body comprises a detachment mechanism having an opening to provide access to a portion of the ultrasound patch probe for removal of the ultrasound patch probe from the bracket probe coupler.

8. The system of claim 1, wherein the selected one of the plurality of ultrasound patch probe brackets includes the single, pre-defined ultrasound acquisition angle of approximately 45 degrees.

9. The system of claim 1, wherein the ultrasound patch probe is detachably coupled to the bracket probe coupler by:
inserting a first side of the ultrasound patch probe into a first side of the bracket probe coupler, and
pivoting a second opposite side of the ultrasound patch probe about the inserted first side of the ultrasound patch probe into a second, opposite side of the bracket probe coupler.

10. The system of claim 1, wherein the ultrasound patch probe is detachably coupled to the bracket probe coupler by sliding the ultrasound patch probe into a slot defined by the bracket probe coupler.

11. The system of claim 1, comprising an adhesive patch attached to the bracket base and configured to detachably couple with the skin of the patient.

12. An ultrasound patch probe bracket, comprising:
a bracket body having a bracket probe coupler and a hollow interior portion, the bracket probe coupler provided at a single, pre-defined angle, the bracket probe coupler operable to receive an ultrasound patch probe at a single, pre-defined ultrasound acquisition angle based on the single, pre-defined angle of the bracket probe coupler, wherein the bracket probe coupler defines a probe opening to provide the ultrasound patch probe access to the hollow interior portion of the bracket body; and
a bracket base surrounding a perimeter of the bracket body and defining a bracket opening that extends through the bracket base to provide access to the hollow interior portion of the bracket body, the bracket base comprising a bottom surface operable to be secured against skin of a patient,
wherein the probe opening, the hollow interior portion, and the bracket opening form an ultrasound acquisition channel for the transmission and reception of ultrasound signals between a transducer surface of the ultrasound patch probe and the skin of the patient if the ultrasound patch probe is detachably coupled to the bracket probe coupler and the bottom surface is secured against the skin of the patient.

13. The ultrasound patch probe bracket of claim 12, comprising an ultrasound gel pad disposed within the hollow interior portion of the bracket body.

14. The ultrasound patch probe bracket of claim 12, wherein the ultrasound gel pad at least partially extends into one or both of the probe opening and the bracket opening.

15. The ultrasound patch probe bracket of claim 12, wherein the bracket probe coupler comprises a first bracket probe cable clearing at a first end of the bracket probe coupler and a second bracket probe clearing at a second opposite end of the bracket probe coupler.

16. The ultrasound patch probe bracket of claim 12, wherein the bracket body comprises a detachment mechanism having an opening to provide access to a portion of the ultrasound patch probe for removal of the ultrasound patch probe from the bracket probe coupler.

17. The ultrasound patch probe bracket of claim 12, wherein the ultrasound patch probe bracket includes the single, pre-defined ultrasound acquisition angle of approximately 45 degrees.

18. The ultrasound patch probe bracket of claim 12, comprising an adhesive patch attached to the bracket base and configured to detachably couple with the skin of the patient.

19. The ultrasound patch probe bracket of claim 12, wherein the bracket probe coupler defines a slot configured to slideably receive the ultrasound patch probe.

20. The ultrasound patch probe bracket of claim 12, wherein the bracket probe coupler comprises:
a first side configured to receive an insertion of a first side of the ultrasound patch probe, and
a second side, opposite the first side, configured to receive a second opposite side of the ultrasound patch probe.

* * * * *